(12) United States Patent
Jensen et al.

(10) Patent No.: US 7,802,642 B2
(45) Date of Patent: Sep. 28, 2010

(54) SYSTEMS, METHODS AND APPARATUS OF MOTORISED INDEPENDENT MAIN-WHEEL DRIVE AND POSITIONING FOR A MOBILE IMAGING SYSTEM

(75) Inventors: Vernon Thomas Jensen, Draper, UT (US); Samuel Lee Alder, Stansbury Park, UT (US)

(73) Assignee: General Electric Company, Schenectady, NY (US)

( * ) Notice: Subject to any disclaimer, the term of this patent is extended or adjusted under 35 U.S.C. 154(b) by 347 days.

(21) Appl. No.: 11/562,831

(22) Filed: Nov. 22, 2006

(65) Prior Publication Data

US 2008/0118036 A1    May 22, 2008

(51) Int. Cl.
*B62D 11/02*    (2006.01)

(52) U.S. Cl. ........................ 180/6.5; 180/6.48

(58) Field of Classification Search ........... 180/6.5, 180/6.48, 6.2
See application file for complete search history.

(56) References Cited

U.S. PATENT DOCUMENTS

| | | | | |
|---|---|---|---|---|
| 4,955,046 A * | 9/1990 | Siczek et al. | ................. | 378/197 |
| 5,499,284 A * | 3/1996 | Pellegrino et al. | ........... | 378/198 |
| 5,583,909 A * | 12/1996 | Hanover | ................... | 378/197 |
| 6,056,074 A * | 5/2000 | Heal et al. | ................. | 180/6.48 |
| 6,131,690 A * | 10/2000 | Galando et al. | ............. | 180/411 |
| 6,374,937 B1 * | 4/2002 | Galando et al. | ............. | 180/211 |
| 6,409,382 B1 * | 6/2002 | Akutsu et al. | ............... | 378/198 |
| 6,609,826 B1 * | 8/2003 | Fujii et al. | ................... | 378/198 |
| 6,705,758 B1 * | 3/2004 | Luusua et al. | ............... | 378/198 |
| 6,729,115 B2 * | 5/2004 | Bartel | ........................ | 56/11.3 |
| 7,213,663 B2 * | 5/2007 | Kim | .......................... | 180/6.5 |

\* cited by examiner

*Primary Examiner*—Lesley Morris
*Assistant Examiner*—Michael R Stabley
(74) *Attorney, Agent, or Firm*—William Baxter, Esq.; Michael G. Smith, Esq.; Ellis B. Ramirez, Esq.

(57) ABSTRACT

Systems, methods and apparatus are provided through which in some embodiments, a mobile imaging device includes one or more motors to propel the mobile imaging device.

17 Claims, 12 Drawing Sheets

SYSTEMS, METHODS AND APPARATUS OF MOTORISED INDEPENDENT MAIN-WHEEL DRIVE AND POSITIONING FOR A MOBILE IMAGING SYSTEM

FIELD OF THE INVENTION

This invention relates generally to mobile imaging systems, and more particularly to transportation of the mobile imaging systems.

BACKGROUND OF THE INVENTION

Mobile fluoroscopy "C-arm" systems are used in radiology departments and operating rooms (ORs) throughout the world. Quite often, the C-arm systems are required to be operated in different locations within a medical facility or different locations in a room. The C-arm systems are steered and maneuvered during transport from one location to another in mostly a "forward" direction.

Improved ease-of-transport and maneuverability continue to be high on the list of needed improvements. As mobile C-arm systems approach the equivalent functional features and image quality of fixed-room fluoroscopic X-ray systems, (counter to the goal of improved maneuverability), mobile C-arm systems are becoming larger and heavier. Higher power X-ray generators, higher capacity X-ray tubes, and flat panel solid state X-ray detectors requiring on-board cooling solutions, all bring the mobile C-arm one step closer to state-of-the-art fixed-room system performance, but also increase the size, and significantly increases the weight. Maneuvering the C-arm systems is becoming more and more difficult as the C-arm systems become heavier.

The most recent C-arm systems weigh more than 700 lbs. The next generation of C-arm systems will weigh even more. "O-Arm" devices can weight two or three times as much as a C-arm. In the environment where the C-arm systems are normally used, mobile C-arms may be moved from room-to-room several times in a day. It is not uncommon to move the mobile C-arm systems between a radiology department and the surgery department, which are often on different levels in a hospital. Pushing the mobile C-arm system can be a physical challenge for people of large stature, but is even more difficult for people of smaller stature.

Carpeted floors are not uncommon in healthcare facilities, and are becoming increasingly common. Pushing the mobile C-arm systems across carpeted surfaces is difficult.

For the reasons stated above, and for other reasons stated below which will become apparent to those skilled in the art upon reading and understanding the present specification, there is a need in the art for improved ease of transportation of mobile fluoroscopy C-arm systems, or other mobile imaging systems.

BRIEF DESCRIPTION OF THE INVENTION

The above-mentioned shortcomings, disadvantages and problems are addressed herein, which will be understood by reading and studying the following specification.

In one aspect, a mobile imaging apparatus includes a base and a plurality of large-diameter main wheels mounted on the base. The large main wheels reduce the horizontal force that is required to move the mobile imaging system, which solves the need in the art for improved ease of transportation of mobile imaging systems.

In another aspect, a mobile imaging apparatus includes a base, a plurality of main wheels that are mounted on the base and at least one electric motor that is operably coupled to the main wheels. The motor reduces the horizontal force that is required to move the mobile imaging system, which solves the need in the art for improved ease of transportation of mobile imaging systems.

In yet another aspect, a mobile imaging apparatus includes one electric motor for each of the main wheels. In some embodiments, the main wheels can operate independently, and in opposite directions or at different speeds which allows the mobile imagining device to move in all motions, including straight line and in an infinite variety of curved paths including rotation in place.

In still another aspect, a mobile imaging apparatus includes a clutch between each electric motor and main wheel.

In a further aspect, a mobile imaging apparatus includes a battery to power the electric motor(s).

In yet a further aspect, a mobile imaging apparatus includes a control apparatus to control speed and direction of the mobile imaging apparatus.

Apparatus, systems, and methods of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, apparatus of embodiments are described. In the third section, embodiments of methods are described. Finally, in the fourth section, a conclusion of the detailed description is provided.

System Level Overview

Figure 1:
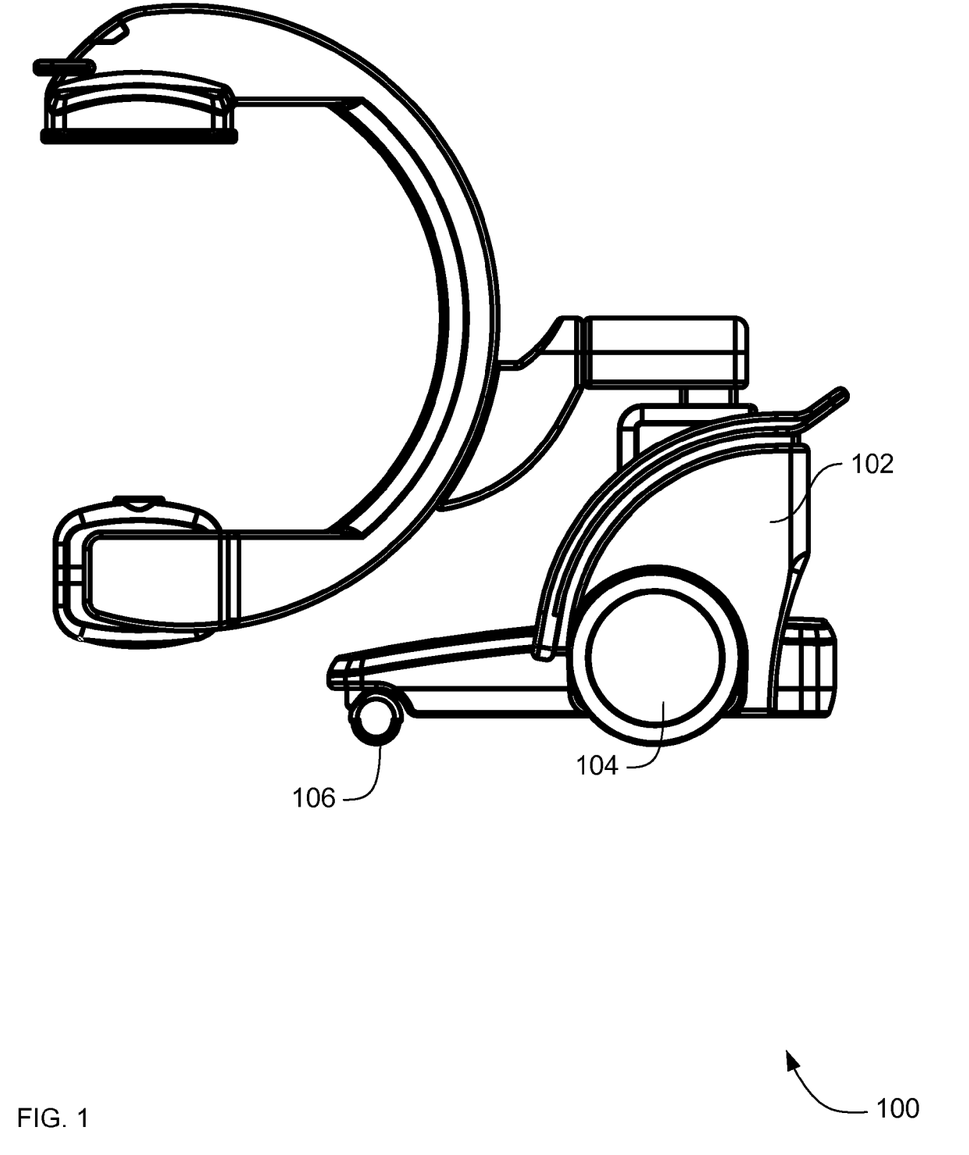
FIG. 1 is a side-view diagram of an overview of a mobile imaging system, according to an embodiment.

A system level overview of the operation of an embodiment is described in this section of the detailed description. FIG. 1 is a side-view diagram of an overview of a mobile imaging system 100, according to an embodiment. Mobile imaging system 100 solves the need in the art for improved ease of transportation of mobile imaging systems.

Mobile imaging system 100 includes a base 102 and a plurality of large main wheels 104 that are mounted on the base 102. The large main wheels reduce the horizontal force that is required to move the mobile imaging system 100. In particular, the large main wheels 104 spread over a larger area the weight of the mobile imaging system 100 that is supported by the large main wheels 104, and thus both static and dynamic friction of the large main wheels 104 with the floor is reduced. In addition, the large main wheels improve the maneuverability of the mobile imaging system 100 in rolling over small obstacles on the floor, such as bumps or other anomalies in the floor and abrupt transitions and thresholds in the floor at the entrance to elevators and doorways.

One example of large main wheels 104 are wheels that have a diameter of about ten to twenty-five inches. A more specific example of large main wheels 104 are wheels that have a diameter of about fifteen to eighteen inches, as shown in FIG. 1. However, the mobile imaging system 100 is not limited to main wheels 104 having a diameter of about fifteen to eighteen inches. Mobile imaging system 100 includes all main wheels 104 that are larger than the conventional main wheels of diameter of about seven or eight inches.

One example of a mobile imaging system is a mobile fluoroscopy C-arm system, as shown in FIG. 1. Some embodiments of mobile imaging system 100 also include one or more castered wheel(s) 106 mounted on the base 102. The castered wheel(s) 106 are mounted forward of the plurality of large main wheels 104.

While the mobile imaging system 100 is not limited to any particular base 102, large main wheels 104 and castered wheel(s) 106, for sake of clarity a simplified base 102, large main wheels 104 and castered wheel(s) 106 are described.

Apparatus Embodiments

In the previous section, a system level overview of the operation of an embodiment was described. In this section, the particular apparatus of such an embodiment are described by reference to a series of diagrams.

Figure 2:
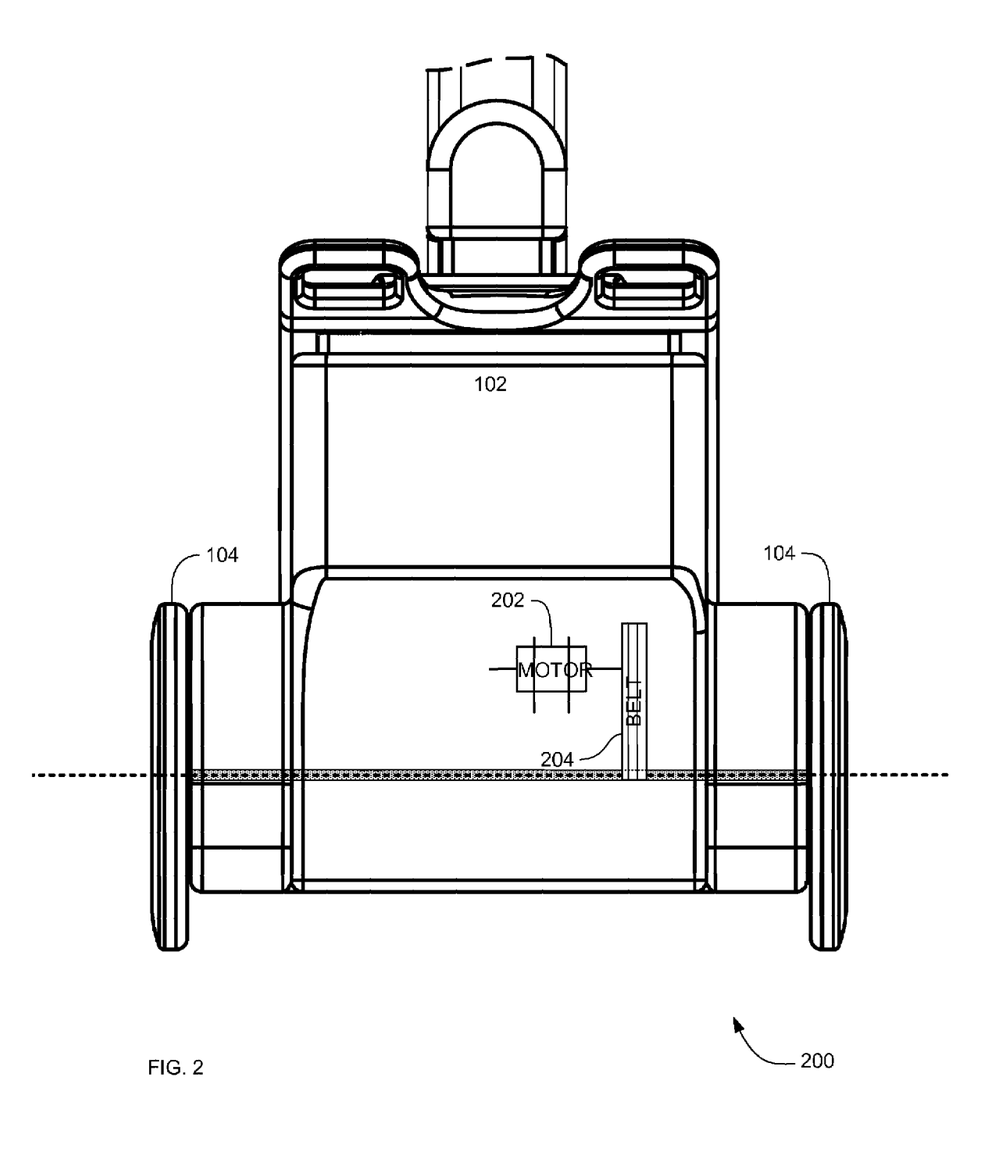
FIG. 2 is an enlarged rear-view diagram of a portion of a mobile imaging system, according to an embodiment having a motorized propulsion system.

FIG. 2 is an enlarged rear-view diagram of a portion of a mobile imaging system 200, according to an embodiment having a motorized propulsion system. Mobile imaging system 200 solves the need in the art for improved ease of transportation of mobile imaging systems.

The mobile imaging system 200 includes a base 102 having a plurality of main wheels 104 mounted on the base 102. The mobile imaging system 200 also includes one or more electric motor(s) 202 or other source of mechanical energy. The electric motor 202 is operably coupled to the main wheels 104 through a belt 204 or other drive train or transmission.

Figure 3:
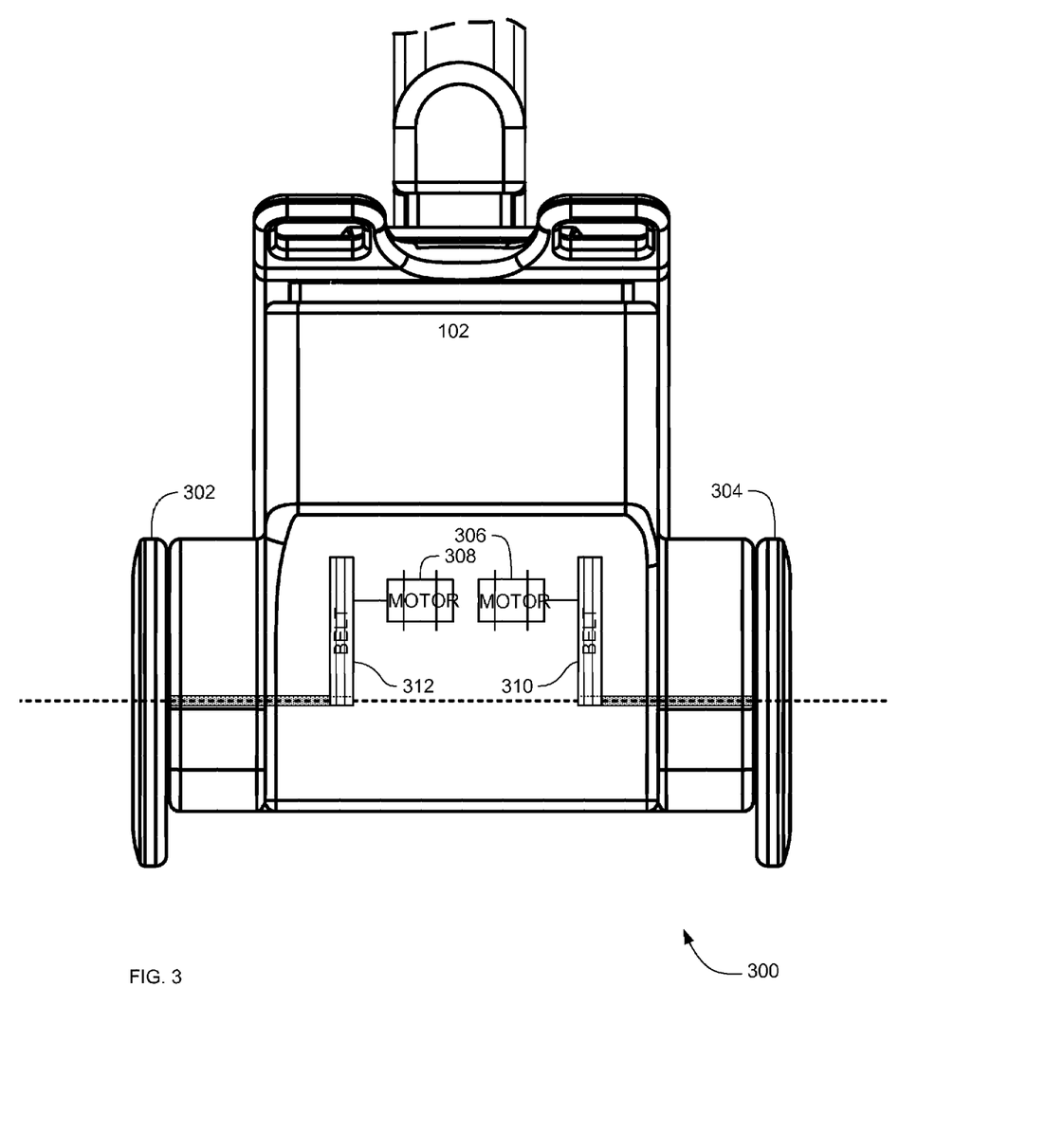
FIG. 3 is an enlarged rear-view diagram of a portion of a mobile imaging system, according to an embodiment wherein the main wheels are independently motorized.

FIG. 3 is an enlarged rear-view diagram of a portion of a mobile imaging system 300, according to an embodiment wherein the main wheels are independently motorized. Mobile imaging system 300 solves the need in the art for improved ease of transportation of mobile imaging systems.

In mobile imaging system 300, the plurality of main wheels 104 include two main wheels 302 and 304. System 300 also includes two electric motors, a first electric motor 306 that is operably coupled to main wheel 304, and a second electric motor 308 that is operably coupled to main wheel 308.

Each electric motor is operable to provide force that propels the mobile imaging system 300 in an opposite direction to the other electric motor. Thus the two electric motors 306 and 308 are operable to rotate the mobile imaging device 308 in place in a horizontal plane. For example, when electric motor 306 drives main wheel 304 in a forward direction, and electric motor 308 drives main wheel 302 in a backward direction, the mobile imaging system 300 will rotate in about the same place on the floor. The independently powered main wheels is particularly helpful as a means to transport the mobile imaging system 300 in any path that other than straight backwards and straight forwards, which improves ease of transportation of mobile imaging systems.

The electric motor 306 is operably coupled to the main wheel 304 through a belt 310 or other drive train or transmission and electric motor 306 is operably coupled to the main wheel 304 through a belt 312 or other drive train or transmission.

In some embodiments, electric motor 306 is a smaller motor than electric motor 202 because electric motor 306 powers only one main wheel 304, while electric motor 202 powers a plurality of main wheels 104.

Figure 4:
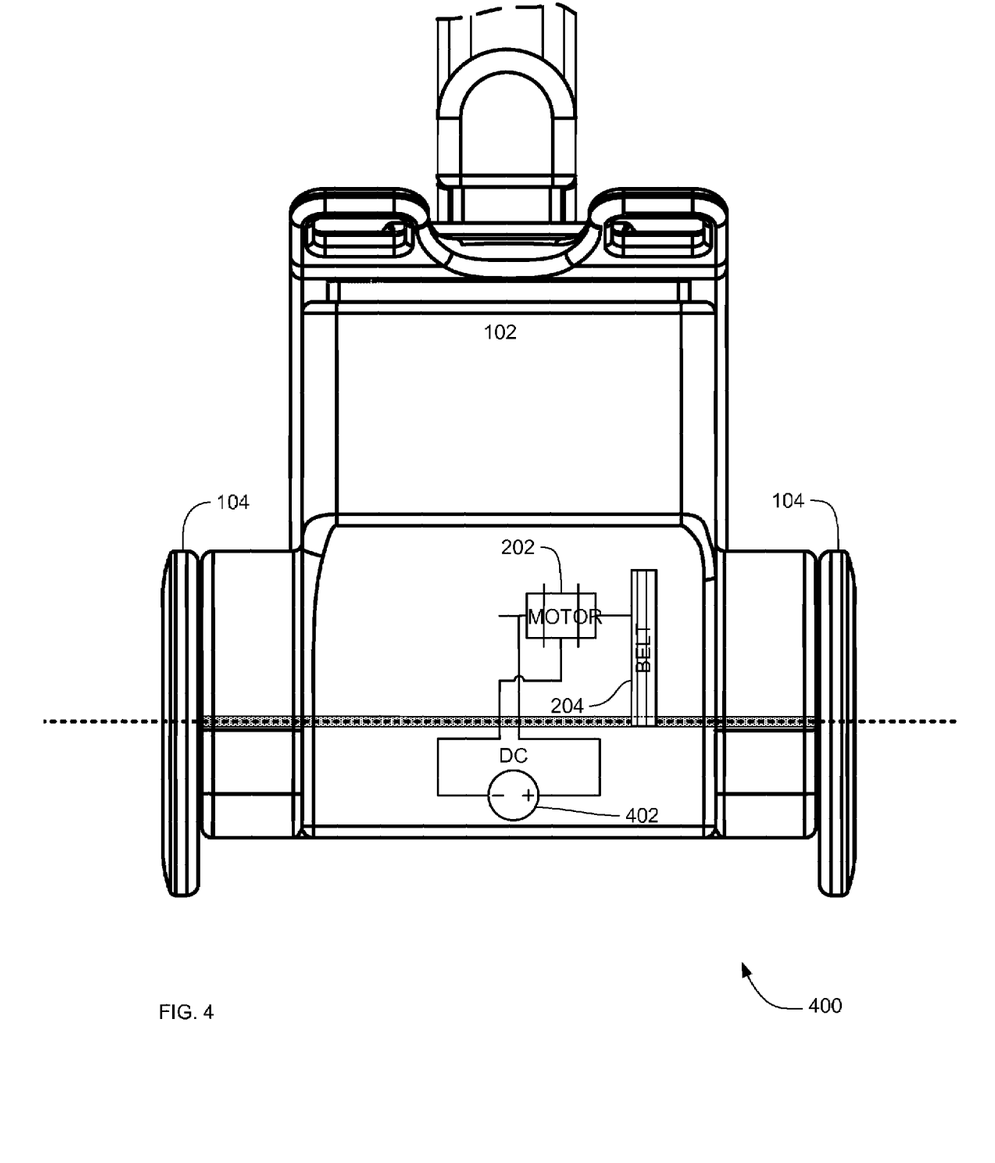
FIG. 4 is an enlarged rear-view diagram of a portion of a mobile imaging system, according to an embodiment having a battery.

FIG. 4 is an enlarged rear-view diagram of a portion of a mobile imaging system 400, according to an embodiment having a battery. Mobile imaging system 400 solves the need in the art for improved ease of transportation of mobile imaging systems.

Mobile imaging system 400 includes one or more batteries 402 that are operably coupled to the electric motor 202. The battery 402 provides a mobile power source as an alternative to an external corded alternating current (A/C) power source (not shown). The battery 402 eliminates the need to connect to an external power source for as long as the battery 402 holds a charge, which improves ease of transportation of mobile imaging systems.

Figure 5:
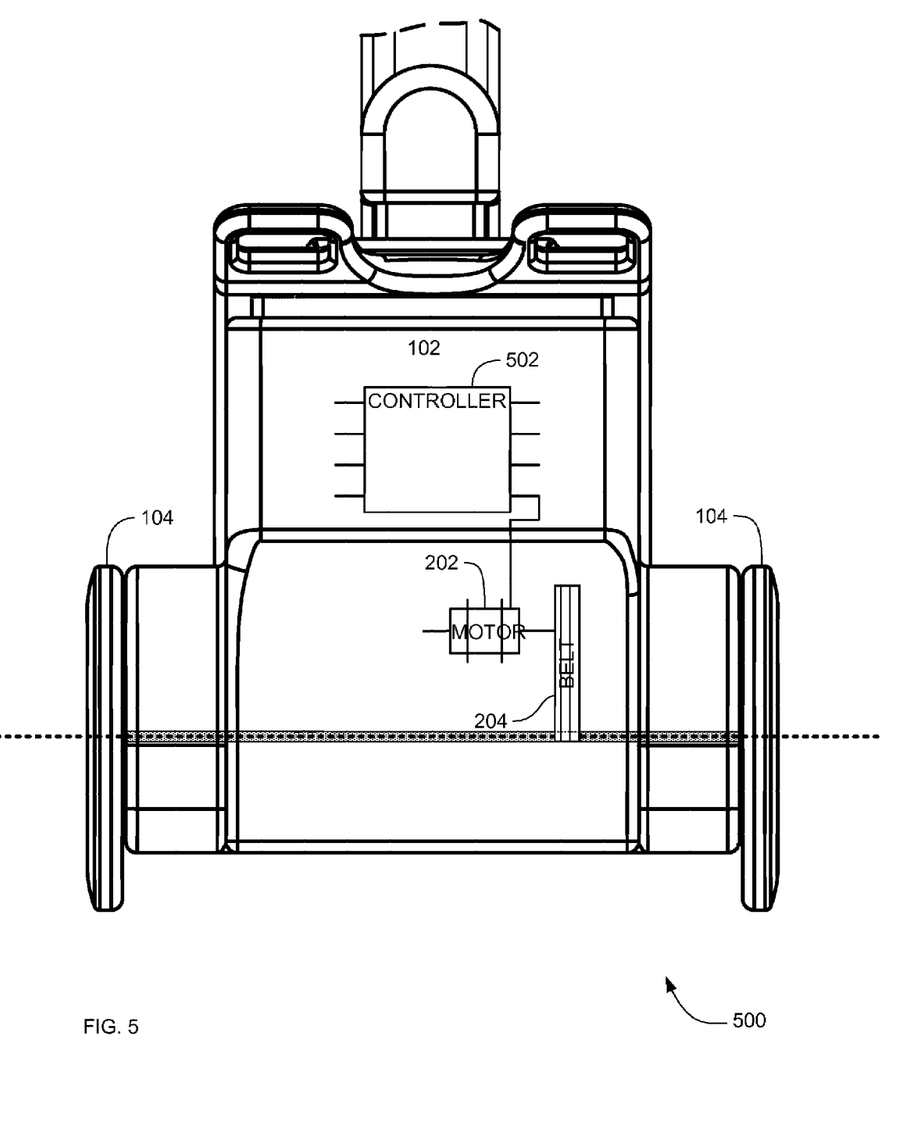
FIG. 5 is an enlarged rear-view diagram of a portion of a mobile imaging system, according to an embodiment having an apparatus to control the motorized propulsion system.

FIG. 5 is an enlarged rear-view diagram of a portion of a mobile imaging system 500, according to an embodiment having an apparatus to control the motorized propulsion system. Mobile imaging system 500 solves the need in the art to improve ease of transportation of mobile imaging systems.

Mobile imaging system 500 includes one of more control apparatus(s) 502 that is operably coupled to the one or more electric motor(s) 202 to actuate and control the main wheels 104. In some embodiments, the control apparatus 502 is a microprocessor (not shown) that is operable to actuate and control the main wheels.

Figure 6:
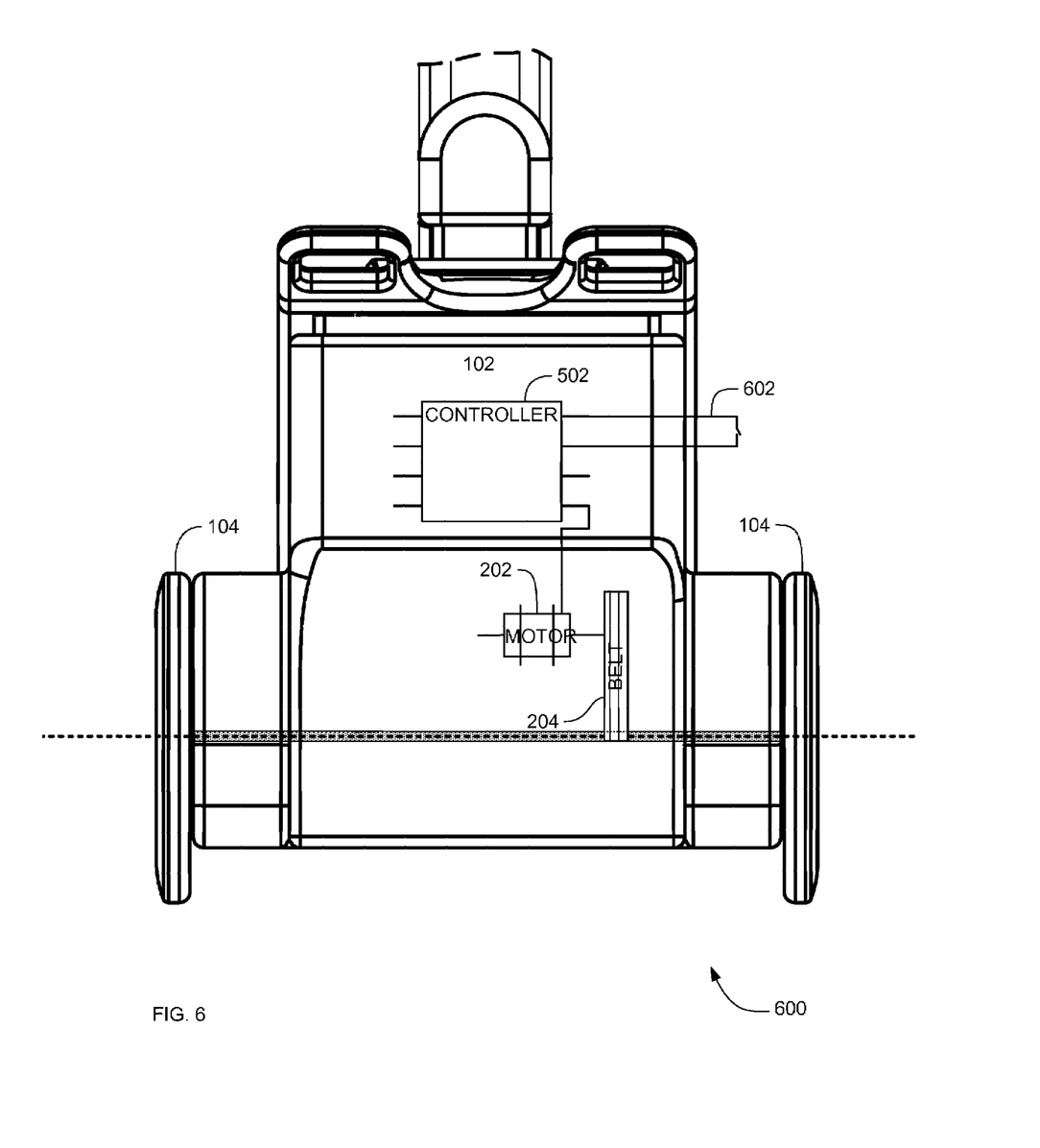
FIG. 6 is an enlarged rear-view diagram of a portion of a mobile imaging system, according to an embodiment having a switch to control the motorized propulsion system.

FIG. 6 is an enlarged rear-view diagram of a portion of a mobile imaging system 600, according to an embodiment having a switch 602 to control the motorized propulsion system. Mobile imaging system 600 includes an activate/deactivate switch 602 that is operably coupled to the control apparatus 502 to actuate and control the main wheels 104.

Figure 7:
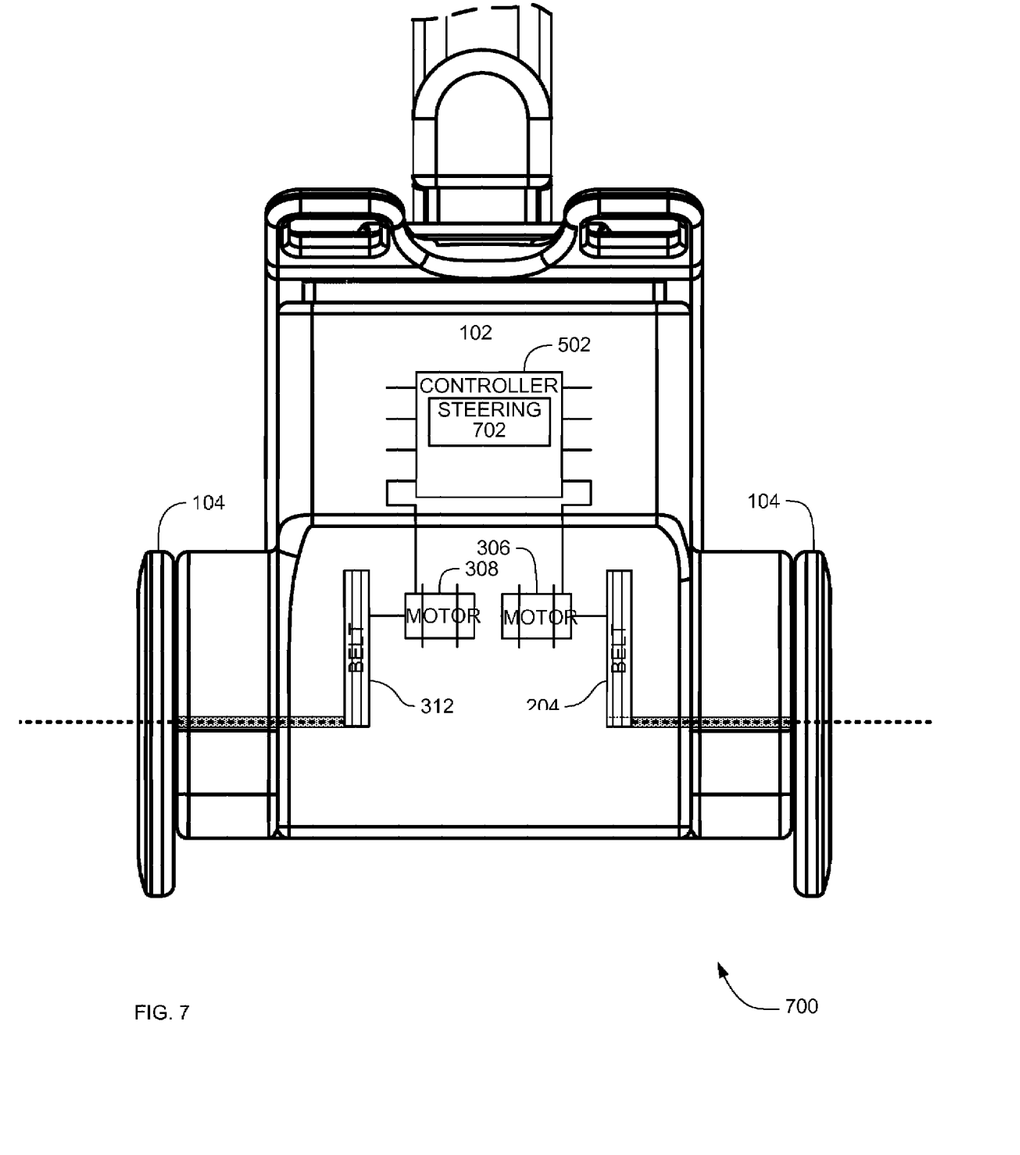
FIG. 7 is an enlarged rear-view diagram of a portion of a mobile imaging system, according to an embodiment having a steering control.

FIG. 7 is an enlarged rear-view diagram of a portion of a mobile imaging system 700, according to an embodiment having a steering control. Mobile imaging system 700 solves the need in the art to improve ease of transportation of mobile imaging systems.

Mobile imaging system 700 includes a steering control 702 to direct the direction of movement of the mobile imaging system 700 through the main wheels 104 by directing force to the main wheels 104 through the plurality of electric motor(s) 306 and 306. Steering the mobile imaging system 700 increases the ease of transportation of the mobile imaging system 700.

Figure 8:
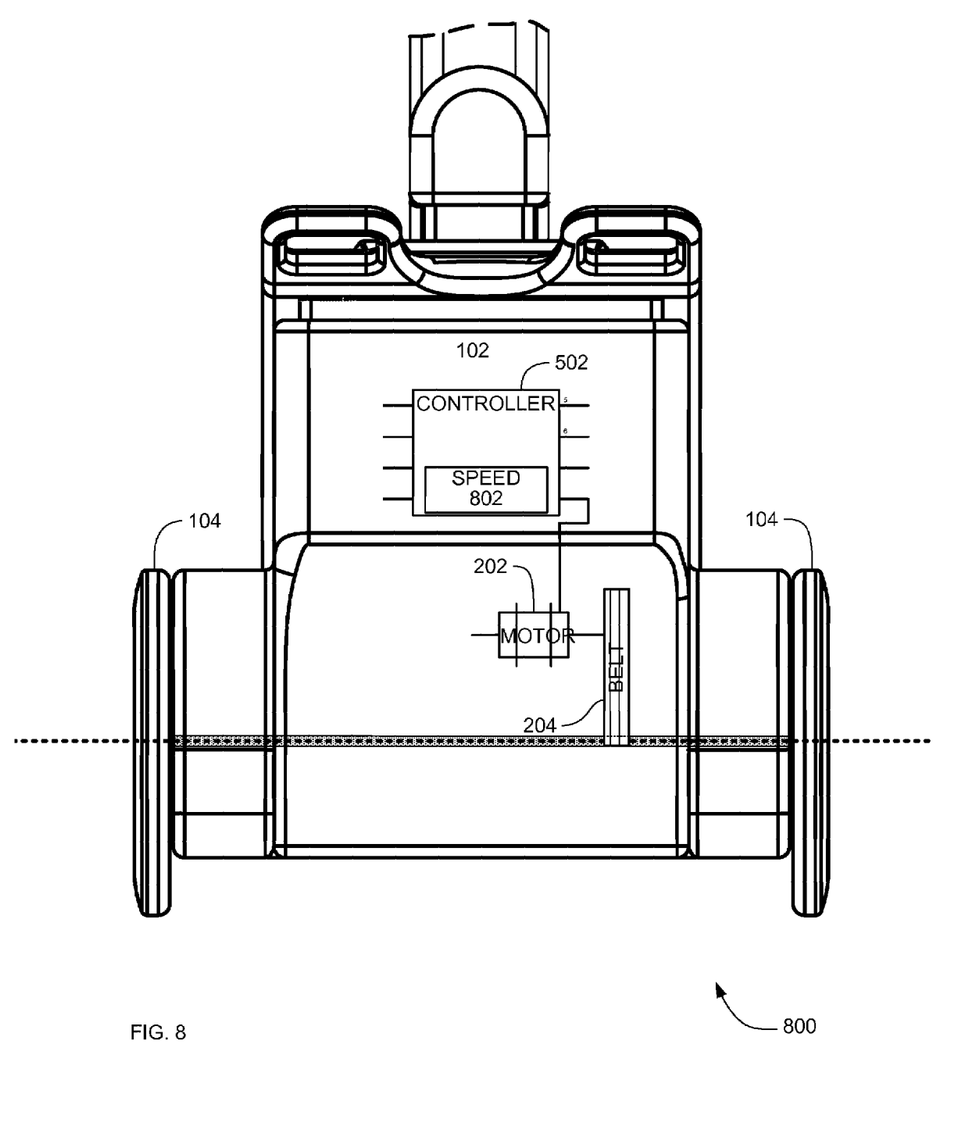
FIG. 8 is an enlarged rear-view diagram of a portion of a mobile imaging system, according to an embodiment having a speed control.

FIG. 8 is a rear-view block diagram of mobile a portion of a mobile imaging system 800, according to an embodiment having a speed control. Mobile imaging system 800 solves the need in the art to improve ease of transportation of mobile imaging systems.

Mobile imaging system 800 includes a speed control 802. The speed control 802 is operable to direct the speed of movement of the mobile imaging system 800 through the main wheels 104 by directing force to the main wheels 104 through the one or more electric motor(s) 202.

Figure 9:
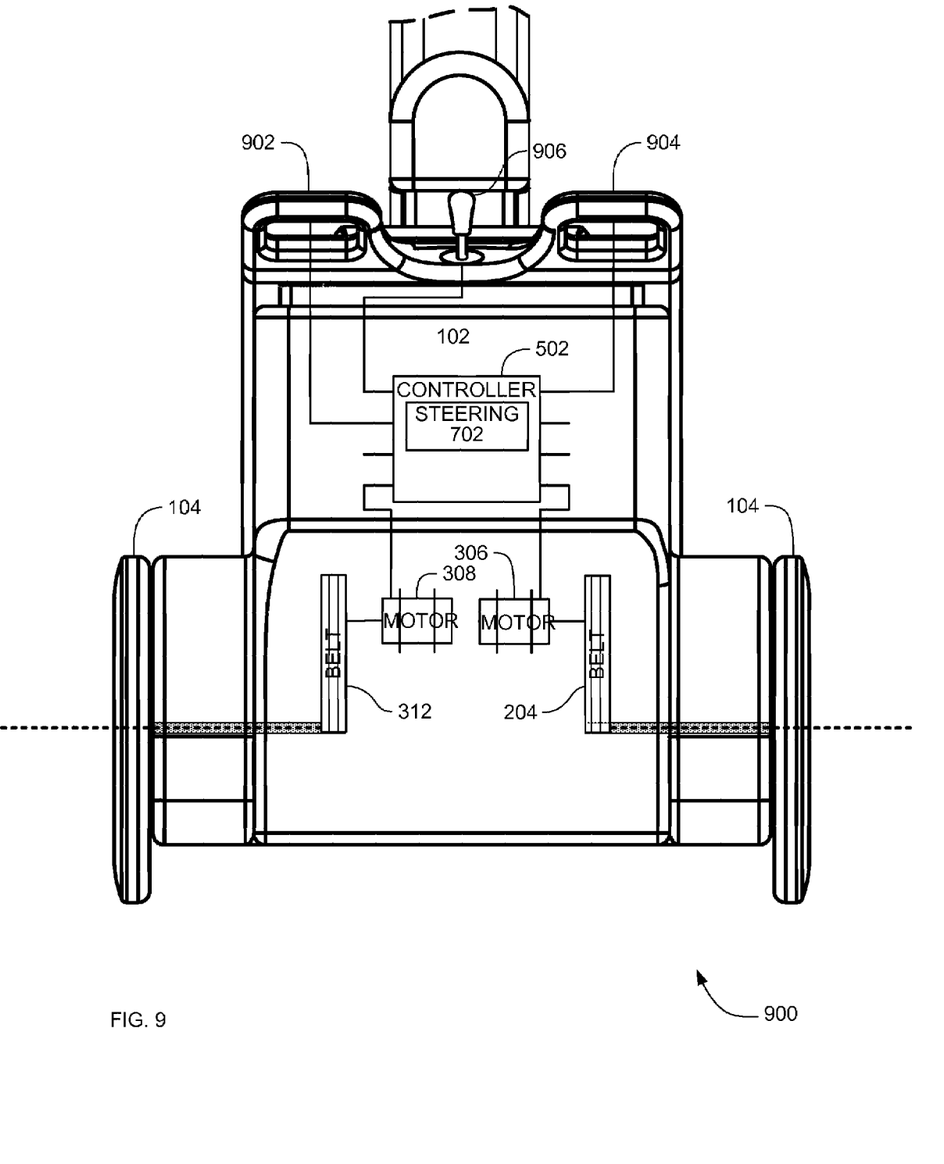
FIG. 9 is an enlarged rear-view diagram of a portion of a mobile imaging system, according to an embodiment having a control apparatus.

FIG. 9 is a rear-view block diagram of mobile a portion of a mobile imaging system 900, according to an embodiment having a control apparatus. Mobile imaging system 900 solves the need in the art to improve ease of transportation of mobile imaging systems.

Mobile imaging system 900 includes one or more force-sensing handle(s). The force sensing handle(s) 902 provide direction for steering the mobile imaging system 900. In some embodiments, one of the force-sensing handle(s) is located on the base 102, which is particularly helpful to an operator guiding the mobile imaging system 900 from the front. In some embodiments where the force-sensing handle(s) are located on the base 102, the force-sensing handle(s) are located in the vicinity of the handles 902 and 904 in which coordination of force applied to the force-sensing handle(s) by the hands of an operator provides direction information to the mobile imaging system 900. In some embodiments where the force-sensing handle(s) are located on the base 102, the force-sensing handle(s) are a joystick 904 located in the top of the base 102 in which force applied to the joystick 906 by the hand of an operator provides direction information to the mobile imaging system 900. In other embodiments, the force-sensing handle(s) are located on a separate electronic device that communicates steering data to the mobile imaging system 900 via a wired communication and/or a wireless communication path.

Figure 10:
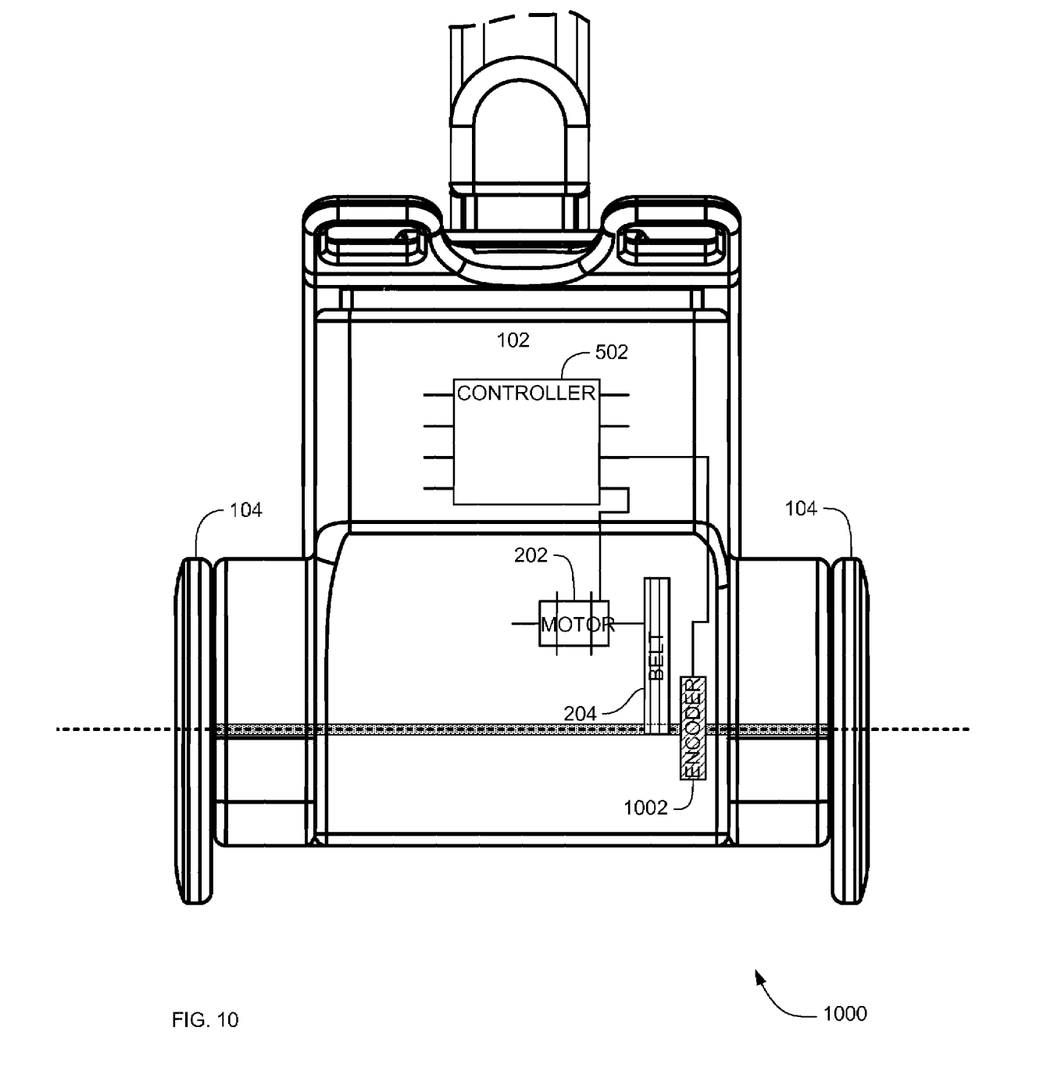
FIG. 10 is an enlarged rear-view diagram of a portion of a mobile imaging system, according to an embodiment having encoders.

FIG. 10 is a rear-view block diagram of mobile a portion of a mobile imaging system 1000, according to an embodiment having encoders. Mobile imaging system 1000 solves the need in the art to improve ease of transportation of mobile imaging systems.

Mobile imaging system 1000 includes one more position encoder(s) 1002 operably coupled to each of the main wheel(s) 104. The encoder(s) 1002 are operable to determine a position of the mobile imaging system 1000. The control apparatus 502 is operable to receive data describing the position of the main wheels 104 and the control apparatus 502 is operable to control the one ore more electric motor(s) 202 to move the mobile imaging system 1000 between a location position and other locations. The encoder(s) 1002 improve the maneuverability of the mobile imaging system 1000, which in turn improves ease of transportation of mobile imaging systems.

Figure 11:
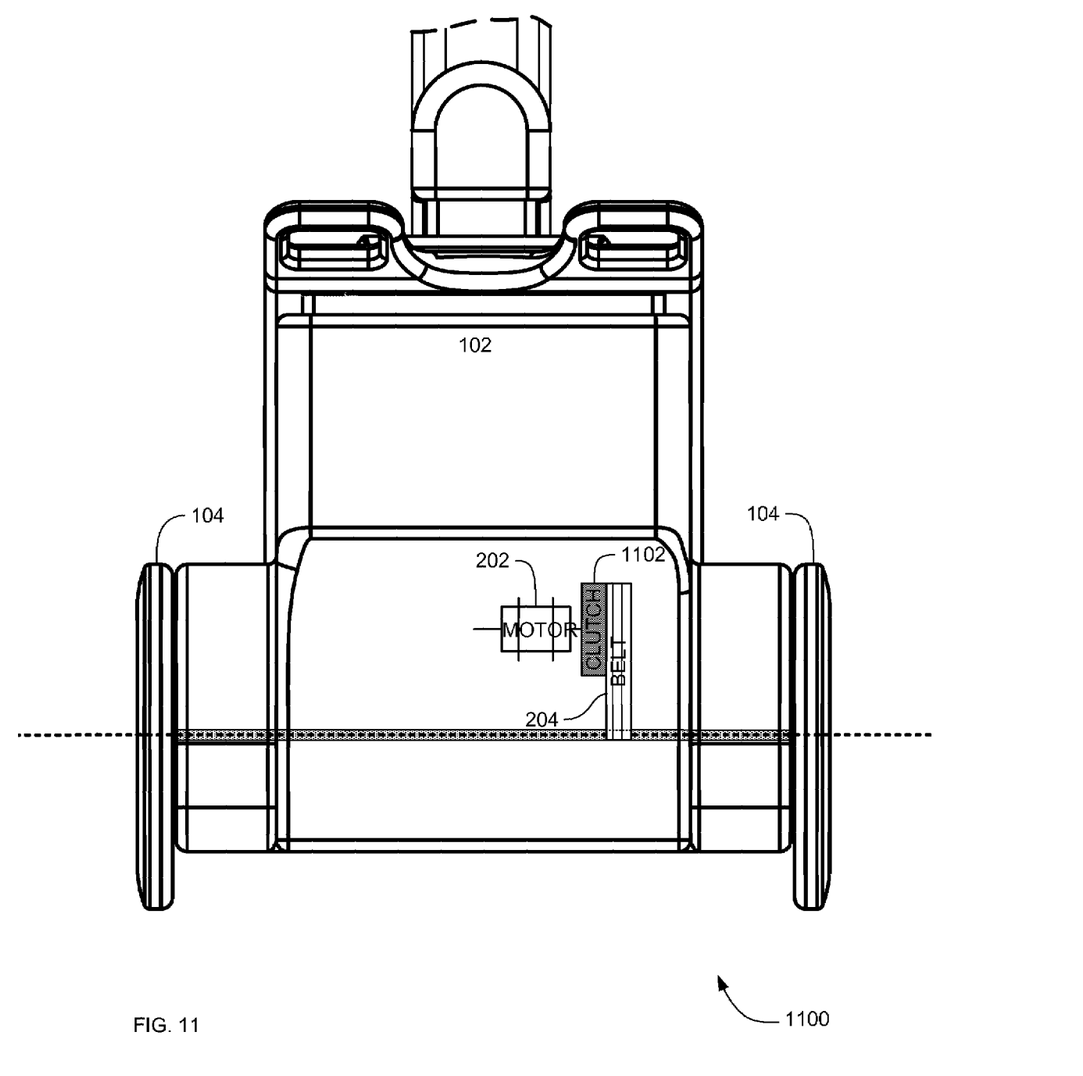
FIG. 11 is an enlarged rear-view diagram of a portion of a mobile imaging system, according to an embodiment having a clutch.

FIG. 11 is a rear-view block diagram of mobile a portion of a mobile imaging system 1100, according to an embodiment having a clutch. Mobile imaging system 1100 solves the need in the art to improve ease of transportation of mobile imaging systems.

Mobile imaging system 1100 includes one or more clutch(s) 1102. The clutch(s) 1102 are operably coupled to the plurality of main wheels 105 and the one or more electric motor(s) 202. The clutch(s) 1102 are located in between the main wheel(s) 104 and the one or more electric motor(s) 104. The clutch(s) 1102 are operable to disengage the main wheels 104 and the one or more electric motor(s) 202. Disengaging the main wheels from the electric motors is helpful when the electrics are disabled, so that the mobile imaging system 1100 can be manually pushed across the floor.

Some embodiments of mobile imaging system 1100 also include a precise low-gear (not shown). The precise low-gear is operably coupled to the main wheel(s) 104 and the one or more electric motor(s) 202. The precise low-gear is located in between the main wheel(s) 104 and the one or more electric motor(s) 202.

Figure 12:
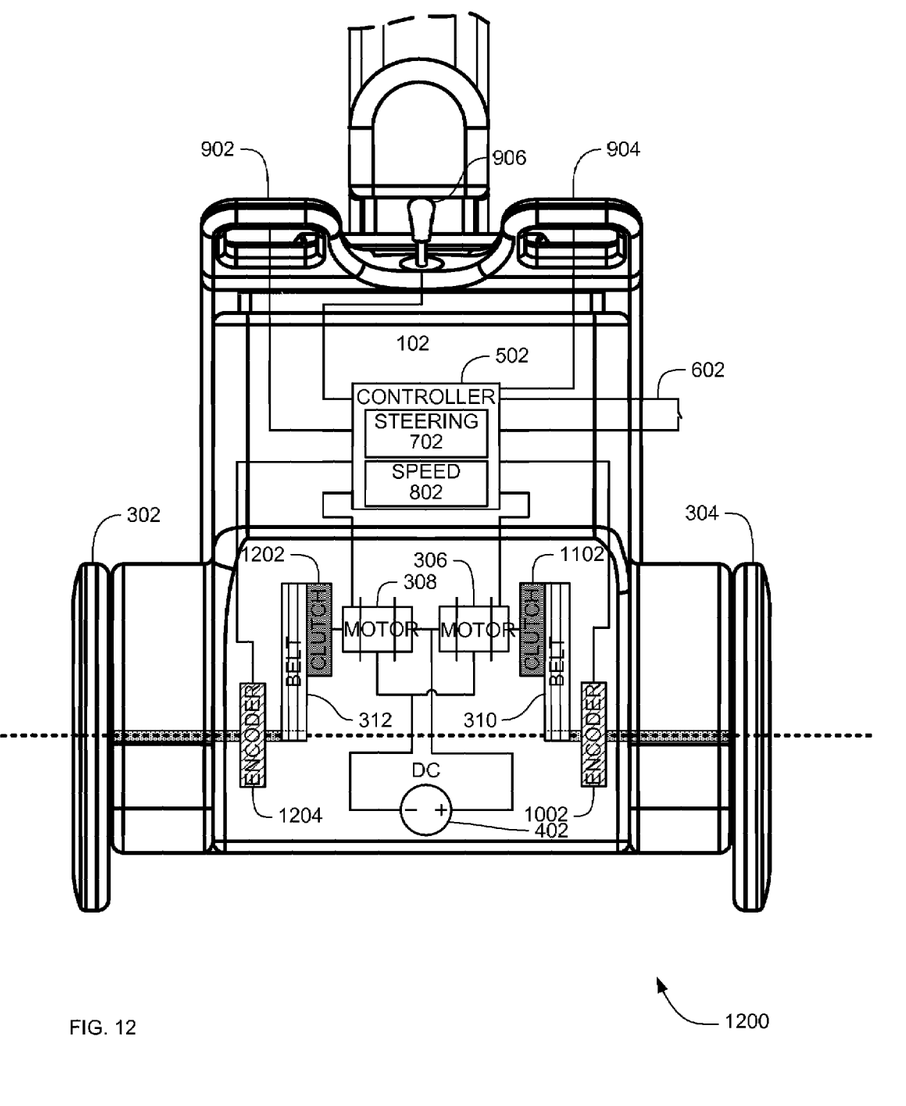
FIG. 12 is an enlarged rear-view diagram of a portion of a mobile imaging system, according to an embodiment having one electric motor that operates independently for each of the main wheels, a clutch between each electric motor and main wheel, a battery to power the electric motor(s), and a control apparatus to control speed and direction of the mobile imaging system.

FIG. 12 is a rear-view block diagram of mobile a portion of a mobile imaging system 1200, according to an embodiment having one electric motor that operates independently for each of the main wheels, a clutch between each electric motor and main wheel, a battery to power the electric motor(s), a control apparatus to control speed and direction of the mobile imaging system. System 1200 is a virtual robot with almost unlimited automated positioning opportunities. System 1200 automatically determines imaging trajectories, and performs motion scans. Mobile imaging system 1200 solves the need in the art to improve ease of transportation of mobile imaging systems.

Mobile imaging system 1200 includes a base 102. Mobile imaging system 1200 also includes a first main wheel 304 that is mounted on the base 102 and a second main wheel 302 that is mounted on the base 102.

Mobile imaging system 1200 includes a first electric motor 306 that is operably coupled to first main wheel 304, and a second electric motor 308 that is operably coupled to the second main wheel 302.

Mobile imaging system 1200 includes a first clutch 1102 that is operably coupled to the first main wheel 304 and the first electric motor 306 in between the first main wheel 304 and the first electric motor 306. The first clutch 1102 is operable to disengage the first main wheel 304 and the first electric motor 306.

Mobile imaging system 1200 includes a second clutch 1202 that is operably coupled to the second main wheel 302 and the second electric motor 308 in between the second main wheel 302 and the second electric motor 308. The second clutch 1202 is operable to disengage the second main wheel 302 and the second electric motor 308.

Mobile imaging system 1200 includes a battery 402 that is operably coupled to the first electric motor 306 and that is operably coupled to the second electric motor 308.

Mobile imaging system 1200 includes at least one control apparatus 502 that is operably coupled to the first electric motor 306 and that is operably coupled to the second electric motor 308 to actuate and control the first main wheel 304 and the second main wheel 302. The control apparatus 502 includes a steering control 702 to direct the direction of movement of the mobile imaging system 1200 through the main wheels 304 and 302 by directing force to the electric motors 304 and 302 through the main wheels. The control apparatus 502 also includes a speed control 802 to direct the speed of movement of the mobile imaging system 1200 through the main wheels 304 and 302 by directing force to the main wheels 304 and 302 through the electric motors 306 and 308. The control apparatus 502 is a microprocessor that is operable to actuate and control the main wheels 302 and 306.

In mobile imaging system 1200, each electric motor 306 and 308 is also operable to provide force that propels the mobile imaging system 1200 in an opposite direction to the other electric motor, thus the two electric motors 306 and 308 are operable to rotate the mobile imaging system 1200 in place in a horizontal plane.

Some embodiments of the mobile imaging system 1200 also include an activate/deactivate switch 602 that is operable to actuate and control the main wheels 304 and 302. Some embodiments of the mobile imaging system 1200 also include a control mechanism located on the base.

Some embodiments of the mobile imaging system 1200 also include one or more encoder(s) 1002 and 1204 on each of the main wheels 304 and 302, respectively. The encoders 1002 and 1204 are operable to determine a position of the mobile imaging system 1200. The control apparatus 502 also is operable to receive data describing the position and to control the electric motors 306 and 308 to move the mobile imaging system 1200 between the position and other locations.

Some embodiments of the mobile imaging system 1200 also includes a precise low-gear that is operably coupled to the main wheels 304 and 302 and the electric motors 306 and 308 in between the main wheels 304 and 302 and the electric motors 306 and 308.

In some embodiments that include clutches 1102 and 1202, encoders 1002 and 1204 and controller 502, the clutches 1102 and 1202 are operable as a replacement to a brake on the wheels or as an alternative or adjunct to the brake on the wheel. In those embodiments, force applied to the main wheels is varied by engagement/disengagement and/or partial engagement of the clutch in order to maintain a fixed position of the imaging device. The amount of force required to maintain a fixed position is determined by the controller 502 using data from the encoders 1002 and 1204. The encoders 1002 1204 provide information on the position over time, and thus movement, of the main wheels. When movement of the main wheels is determined, countering forces are provided by the motors 306 and 308 through the clutches to the main wheels to maintain a steady position. Accordingly, some embodiments of the mobile imaging system do not include a brake.

Some embodiments of the above systems and apparatus provide sufficiently precise and easy movement of the mobile imaging system or other mobile imaging system that the system doe not includes a horizontal cross-arm, which is used in conventional systems to guide and position the C-arm assembly. Absence of the horizontal cross-arm reduces "play" (movement or space for movement) of the C-arm assembly.

The actions of control apparatus 502 are implemented as a computer data signal embodied in a carrier wave, that represents a sequence of instructions which, when executed by a processor cause the processor to perform the respective method. In other embodiments, the actions of control apparatus 502 are implemented as a computer-accessible medium having executable instructions capable of directing a processor, to perform the respective method. In varying embodiments, the medium is a magnetic medium, an electronic medium, or an optical medium.

A wide variety of computer hardware and computing environments are suitable to implement the control apparatus. Some embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment. The computer hardware includes a processor that is commercially available from Intel, Motorola, Cyrix and others. The computer hardware also includes random-access memory (RAM), read-only memory (ROM), and optionally one or more mass storage devices. The memory and mass storage devices are types of computer-accessible media. The processor executes computer programs stored on the computer-accessible media.

CONCLUSION

A motorized imaging device is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in any other configuration that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future imaging devices, different control apparatus, and new wheels.

The terminology used in this application is meant to include all microprocessor and imaging environments and alternate technologies which provide the same functionality as described herein.

We claim:

1. A mobile imaging apparatus comprising:
   a base;
   a plurality of large-diameter main wheels mounted on the base;
   at least one electric motor operably coupled to the main wheels;
   at least one control apparatus operably coupled to the at least one electric motor to actuate and control the main wheels, and
   at least one encoder on each of the plurality of large-diameter main wheels, each encoder operable to determine a position of the mobile imaging system,
   wherein the control apparatus is operable to receive data describing the position and determine an amount of force required to maintain a fixed position from data from the at least one encoder,
   wherein each electric motor operable to provide force that propels the mobile imaging apparatus in an opposite direction to the other electric motor, thus the electric motors are operable to rotate the mobile imaging device in place in a horizontal plane.

2. The mobile imaging apparatus of claim 1, wherein the large-diameter main wheels further comprise:
a plurality large-diameter main wheels, each wheel having a diameter of greater than about eight inches.

3. The mobile imaging apparatus of claim 1 further comprising:
a plurality of castered wheels mounted on the base and mounted forward of the plurality of main wheels.

4. The mobile imaging apparatus of claim 1, wherein the mobile imaging apparatus further comprises:
a mobile fluoroscopy C-arm system.

5. A mobile imaging apparatus comprising:
a base;
a plurality of main wheels mounted on the base;
at least one electric motor operably coupled to the main wheels;
at least one control apparatus operably coupled to the at least one electric motor to actuate and control the main wheels, and
at least one encoder on each of the plurality of large-diameter main wheels, each encoder operable to determine a position of the mobile imaging system,
wherein the control apparatus is operable to receive data describing the position and determine an amount of force required to maintain a fixed position from data from the at least one encoders,
wherein each electric motor is operable to provide force that propels the mobile imaging apparatus in an opposite direction to the other electric motor, thus the electric motors are operable to rotate the mobile imaging device in place in a horizontal plane.

6. The mobile imaging apparatus of claim 5, wherein the plurality of main wheels further comprises two main wheels and the at least one electric motor further comprises:
two electric motors, a first electric motor operably coupled to one of the two main wheels and a second electric motor operably coupled to the other one of the two main wheels.

7. The mobile imaging apparatus of claim 5, wherein the two electric motors further comprises:
each electric motor being operable to provide force that propels the mobile imaging apparatus in an opposite direction to the other electric motor, thus the electric motors are operable to move the mobile imaging device in all motions in a horizontal plane, including straight line and in an infinite variety of curved paths.

8. The mobile imaging apparatus of claim 5 further comprising:
a battery operably coupled to the electric motor.

9. The mobile imaging apparatus of claim 5, wherein the control apparatus further comprises:
an activate/deactivate switch that is operably coupled to actuate and control the main wheels.

10. The mobile imaging apparatus of claim 5, wherein the control apparatus further comprises:
a steering control to direct the direction of movement of the mobile imaging device through the main wheels by directing force to the main wheels through the at least one electric motor.

11. The mobile imaging apparatus of claim 5, wherein the control apparatus further comprises:
a speed control to direct the speed of movement of the mobile imaging device through the main wheels by directing force to the main wheels through the at least one electric motor.

12. The mobile imaging apparatus of claim 5 further comprising:
at least one force-sensing handle.

13. The mobile imaging apparatus of claim 5, wherein the at least one force-sensing handle further comprises:
at least one force-sensing handle located on the base.

14. The mobile imaging apparatus of claim 5, wherein the control apparatus further comprises:
a microprocessor operable to actuate and control the main wheels.

15. The mobile imaging apparatus of claim 5, wherein the plurality of main wheels further comprises:
a plurality of large-diameter main wheels mounted on the base.

16. The mobile imaging apparatus of claim 15, wherein the large-diameter main wheels further comprise:
a plurality large-diameter main wheels, each wheel having a diameter of greater than about eight inches.

17. The mobile imaging apparatus of claim 5 further comprising:
a plurality of castered wheels mounted on the base and mounted forward of the plurality of main wheels.

* * * * *